(12) United States Patent
Ogata et al.

(10) Patent No.: US 6,562,543 B2
(45) Date of Patent: May 13, 2003

(54) STABILIZER FOR ORGANIC BORATE SALTS AND PHOTOSENSITIVE COMPOSITION CONTAINING THE SAME

(75) Inventors: Tomonari Ogata, Kawasaki (JP); Tsuyoshi Katoh, Kawasaki (JP); Tomoe Uematsu, Kawasaki (JP); Norihide Arai, Oita (JP); Tomoki Okano, Tokyo (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 09/765,371

(22) Filed: Jan. 22, 2001

(65) Prior Publication Data

US 2001/0046643 A1 Nov. 29, 2001

Related U.S. Application Data

(62) Division of application No. 09/140,832, filed on Aug. 26, 1998, now Pat. No. 6,218,076.
(60) Provisional application No. 60/079,103, filed on Mar. 23, 1998.

(30) Foreign Application Priority Data

Aug. 26, 1997 (JP) ............................................. 9-229376
Jul. 14, 1998 (JP) ........................................... 10-199080

(51) Int. Cl.$^7$ .............................................. G03F 7/027
(52) U.S. Cl. .................... 430/281.1; 430/914; 430/917; 522/31
(58) Field of Search ............................ 430/281.1, 914, 430/270.1, 917

(56) References Cited

U.S. PATENT DOCUMENTS 5,079,126 A    1/1992   Hipps, Sr. et al. ............ 430/138
5,124,235 A *  6/1992   Fukui et al. .................. 430/281
5,141,660 A *  8/1992   Small, Jr. et al. ............ 252/49.6
5,147,758 A    9/1992   Smothers et al. ............. 430/281
5,151,520 A *  9/1992   Gottschalk et al. .......... 548/110
5,153,100 A   10/1992   Weed et al. ................. 430/281
5,160,652 A * 11/1992   Small, Jr. et al. ............ 252/49.6
5,202,039 A *  4/1993   Small, Jr. et al. ............ 252/49.6
5,631,307 A    5/1997   Tanaka et al. ................ 522/25
6,210,863 B1 * 4/2001   Cunningham et al. ..... 430/281.1
6,218,076 B1 * 4/2001   Ogata et al. ............... 430/281.1

OTHER PUBLICATIONS

Chemical Abstracts, vol. 121, No. 18, Oct. 31, 1994, XP–002139194.

Morgan, K.J., "The Alkylation of Mercaptobenzothiazole", XP–002139193, J. Chem. Soc. 1958, 854–858.

\* cited by examiner

*Primary Examiner*—Rosemary Ashton
(74) *Attorney, Agent, or Firm*—Sughrue Mion, PLLC

(57) ABSTRACT

A stabilizer for thermally stabilizing an organic borate salt represented by formula (1) is disclosed, comprising a compound having one or two nitrogen-containing 5- or 6-membered heterocyclic ring having a double bond within the ring, a compound having a primary, secondary or tertiary amino group, or a compound having a thiol group. Also disclosed are a photosensitive composition comprising the stabilizer, an organic borate salt and if desired, a sensitizing dye or further a bisimidazole compound; a polymerizable composition comprising the photosensitive composition having added thereto at least one monomer having one or more ethylenically unsaturated bond and if desired, a high molecular polymer or further a pigment; and a colored pattern formed by using the polymerizable composition.

32 Claims, No Drawings

STABILIZER FOR ORGANIC BORATE SALTS AND PHOTOSENSITIVE COMPOSITION CONTAINING THE SAME

CROSS REFERENCE TO RELATED APPLICATIONS

This is a Divisional application Ser. No. 09/140,832 filed Aug. 26, 1998, U.S. Pat. No. 6,218,076 the disclosure of which is incorporated herein by reference.

This application claims the benefit of provisional application No. 60/079,103 filed on Mar. 23, 1998.

BACKGROUND OF THE INVENTION

1. Field of the Invention

The present invention relates to a stabilizer for preventing the thermal decomposition or reaction of an organic borate salt, a photosensitive composition comprising the stabilizer and an organic borate salt, a polymerizable composition comprising the photosensitive composition having added thereto a monomer having an ethylenically unsaturated bond, which has excellent heat stability and aging stability and is prevented from impairment of the polymerization reactivity, a photopolymerization initiator capable of exhibiting good polymerizability even in the presence of oxygen, and a polymerizable composition containing the photopolymerization initiator.

This application is based on Japanese Patent Applications Nos. Hei 9-229376 and Hei 10-199080, the contents of which are incorporated herein by reference.

2. Description of Related Art

A large number of studies have been made on organic borate salts as an important constituent element of a photopolymerizable composition. Examples thereof include an organic boron compound anion salt of an organic cationic dye (see, JP-A-62-143044 (the term "JP-A" as used herein means an "unexamined published Japanese patent application"), JP-A-64-13141 and JP-A-2-3052) and a system of separately adding an organic cationic dye and an organic borate salt but not adding these in the form of a complex (see, JP-A-2-4804 and JP-A-5-194619). In any of these publications, a photo-polymerizable composition having high photosensitivity obtained by adding a monomer having an ethylenically unsaturated bond to the organic borate salt, is disclosed.

However, these photopolymerizable compositions containing an organic borate salt are not sufficiently high in the heat stability. For example, in a photopolymerizable composition containing an organic borate salt, the organic borate salt gradually decomposes at 0° C. or higher and the decomposition is further accelerated at higher temperatures. As a result of decomposition of the organic borate salt, the photopolymerizable composition is reduced in the photopolymerizability and cannot be cured even with a sufficiently large amount of exposure.

Not only the decomposition of the organic borate salt in the photopolymerizable composition but also unintended polymerization reaction proceed in a dark place. Thus, the photopolymerizable composition is polymerized before exposure and cannot be used any more. Furthermore, as the acidity of the photopolymerizable composition increases, the organic borate salt is extremely reduced in the heat stability and seriously decomposes during the storage.

In order to overcome these problems, attempts have heretofore been made to achieve stabilization by controlling the structure of the organic borate salt, the structure or composition of the sensitizer or monomer having an ethylenically unsaturated bond, or the neutralization of the acidity of the composition. However, satisfactory effects have not yet been achieved.

With respect to the photopolymerizable composition containing a monomer having an ethylenically unsaturated bond and as the photopolymerization initiator system, a titanocene compound and a sensitizer, a photopolymerizable composition further containing a heterocyclic thiol compound so as to achieve stabilization of the titanocene compound is known (see, JP-A-9-5996). However, the effect of improving the stability of the titanocene compound is not yet satisfied.

On the other hand, radiation polymerization using a radiation-sensitive polymerization initiator is being used in various fields such as semiconductor relative, printing ink, printing plate, coating, adhesion and liquid crystal display. The radiation includes high energy radiation such as electron beam and X ray, and low energy radiation such as ultraviolet ray, visible ray and infrared ray, and the radiation is applied by means of a device (lamp) emitting respective rays according to the use purposes. The high energy radiation has a high polymerization initiating capability because of its high energy but is disadvantageous in the complicated apparatus or process necessary therefor, the high use energy and the adverse effects on the environment or an operator. However, due to tendency to use a photopolymerization initiator which generates radicals by light of a low energy radiation such as ultraviolet ray, visible ray or infrared ray, the dangerous high energy radiation is less required. In particular, the photoradical polymerization initiator can polymerize vinyl-base monomers with low energy to thereby promise high sensitivity and high-speed processing and accordingly, is being used very often.

However, it is known that if the radical polymerization is performed in the presence of oxygen, the radicals generated combine with the oxygen to convert into a relatively stable peroxy radicals not having the polymerization initiating capability, whereby the polymerization is inhibited and insufficient polymerization results. This phenomenon is particularly outstanding on the surface of the photopolymerizable composition in contact with air or in the case of a thin film.

To overcome this problem, a method of blocking oxygen by forming an oxygen-blocking film on the surface of the polymerizable composition so as to prevent the effects of oxygen, a method of performing the polymerization by placing the polymerization material as a whole in a nitrogen atmosphere, a method of adding a large amount of a photopolymerization initiator to maintain the sensitivity, a method of adding a tertiary amino compound and generating active radicals from stabilized peroxy radicals to allow the polymerization to proceed, and a method of using a photocationic polymerization initiator and not relying on radicals have heretofore proposed.

However, the above-described methods for overcoming the problem of polymerization inhibition due to oxygen are disadvantageous in that the costs of raw material, process and equipment are greatly increased, the sensitivity is low, the productivity decreases due to complicated processes, and stability or odor of the polymerizable composition or the product after polymerization is another problem. Accordingly, the methods are limited in the use field or usage.

SUMMARY OF THE INVENTION

The present invention has been made to satisfy the requirements for solving the above-described problems.

A first object of the present invention is to provide an excellent stabilizer capable of imparting heat stability to the organic borate salt.

A second object of the present invention is to provide a photosensitive composition comprising this stabilizer and an organic borate salt or comprising this stabilizer, an organic borate salt and a sensitizing dye.

A third object of the present invention is to provide a polymerizable composition comprising the above-described photosensitive composition having added thereto a monomer having an ethylenically unsaturated bond, which is excellent in the heat stability and aging stability and is prevented from impairment of the polymerization reactivity.

A fourth object of the present invention is to provide a high-sensitivity photosensitive composition capable of efficiently initiating photopolymerization even in the presence of oxygen.

As a result of extensive investigations to solve the problems, the present inventors have found that the above-described objects can be attained by using a stabilizer having a specific molecular structure, which not only remarkably improves the stability of the organic borate salt represented by formula (1) having low heat stability but also prevents impairment of the photoreactivity of the polymerizable composition containing the organic borate salt, and further that the photosensitive composition comprising, out of stabilizers of the present invention, a compound having one or two nitrogen-containing 5- or 6-membered heterocyclic ring having a double bond within the ring or a compound having a thiol group and an organic borate salt represented by formula (1) is a high-sensitivity photosensitive composition capable of efficiently initiating photopolymerization even in the presence of oxygen and a photopolymerizable composition comprising this photosensitive composition has high sensitivity even in the presence of oxygen. The present invention has been accomplished based on these findings.

More specifically, the invention provides:

1) A stabilizer for thermally stabilizing an organic borate salt represented by formula (1), comprising a compound having one or two nitrogen-containing 5- or 6-membered heterocyclic ring having a double bond within the ring, a compound having a primary, secondary or tertiary amino group, or a compound having a thiol group:

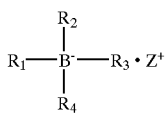

(1)

(wherein $R_1$, $R_2$, $R_3$ and $R_4$ each independently represents an alkyl group, an aryl group, an allyl group, an aralkyl group, an alkenyl group, an alkynyl group, an alkoxy group, a silyl group, an alicyclic group, a heterocyclic group, a hydrogen atom or a halogen atom, and $Z^+$ represents a quaternary ammonium cation, a quaternary pyridinium cation, a quaternary quinolinium cation, a phosphonium cation, a sulfonium cation, an oxosulfonium cation, an oxonium cation, an iodonium cation, a metal cation or a cationic dye having absorption in the ultraviolet and/or visible ray region).

2) A stabilizer for thermally stabilizing an organic borate salt represented by formula (1), comprising a compound having one or two nitrogen-containing 5- or 6-membered heterocyclic ring having a double bond within the ring, a compound having a primary, secondary or tertiary amino group, or a compound having a thiol group:

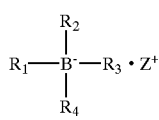

(1)

(wherein $R_1$, $R_2$, $R_3$ and $R_4$ each independently represents an alkyl group, an aryl group, an allyl group, an aralkyl group, an alkenyl group, an alkynyl group, an alkoxy group, a silyl group, a heterocyclic group, a hydrogen atom or a halogen atom, and $Z^+$ represents a quaternary ammonium cation, a quaternary pyridinium cation, a quaternary quinolinium cation, a phosphonium cation, a sulfonium cation, an oxonium cation, an iodonium cation, a metal cation or a cationic dye having absorption in the ultraviolet and/or visible ray region).

3) The stabilizer as described in 1) and 2) above, wherein the compound having one or two nitrogen-containing 5-or 6-membered heterocyclic ring having a double bond within the ring is a compound having one or more heterocyclic ring selected from triazole, pyridine, pyrimidine, pyrazole, piperazine, tetrazole, acridine, adenine, benzothiazole, triazine, thiadiazole, imidazole, benzimidazole, thiazoline, indoline and imidazoline.

4) The stabilizer as described in 1) and 2) above, wherein the compound having a primary, secondary or tertiary amino group is an amine represented by formula (2):

$$R_5R_6R_7N \quad (2)$$

(wherein $R_5$, $R_6$ and $R_7$ each independently represents hydrogen, an alkyl group, an aryl group, an allyl group, an aralkyl group, an alkenyl group, an alkynyl group, a heterocyclic group or an alicyclic group, provided that at least one of $R_5$ $R_6$ and $R_7$ is not hydrogen. Two or three of $R_5$, $R_6$ and $R_7$ may be combined to form a cyclic structure).

5) The stabilizer as described in 1) or 2) above, wherein the compound having a thiol group is a thiol represented by formula (3):

$$R_8\text{—SX} \quad (3)$$

(wherein $R_8$ represents an alkyl group, an aryl group, an aralkyl group, an alkenyl group, an alkynyl group, an alicyclic group or a heterocyclic group, and X represents sodium or hydrogen).

6) A photosensitive composition comprising the stabilizer described in 1) or 2) above and an organic borate salt represented by formula (1).

7) A photosensitive composition comprising the stabilizer described in 1) or 2) above, an organic borate salt represented by formula (1) and a sensitizing dye.

8) The photosensitive composition as described in 6) and 7) above, wherein the stabilizer is a compound having one or two nitrogen-containing 5- or 6-membered heterocyclic ring having a double bond within the ring or a compound having a thiol group.

9) The photosensitive composition as described in 8) above, wherein the stabilizer is at least one selected from mercaptoimidazole, mercaptobenzimidazole, mercaptobenzothiazole, triazinetrithiol, mercaptotriazole, mercaptothiazoline, mercaptothiadiazole and mercaptotetrazole.

10) The photosensitive composition as described in 8) and 9) above, which further contains a bisimidazole compound.

11) A polymerizable composition capable of polymerization by light or heat, comprising the photosensitive composition described in any one of 6) to 10) above having added thereto at least one monomer having one or more ethylenically unsaturated bond.

12) A polymerizable composition comprising the photosensitive composition described in any one of 6) to 10) above having added thereto at least one monomer having one or more ethylenically unsaturated bond and a high molecular polymer.

13) A polymerizable composition comprising the photosensitive composition described in any one of 6) to 10) above having added thereto at least one monomer having one or more ethylenically unsaturated bond, a pigment and a high molecular polymer.

14) The polymerizable composition as described in 12) and 13) above, wherein the high molecular polymer has an acid value of from 20 to 800 mgKOH/g.

15) A colored pattern formed on a substrate using a polymerizable composition described in any one of 11) to 14) above.

DESCRIPTION OF THE PREFERRED EMBODIMENTS

Representative examples of the stabilizer comprising a compound having one or two nitrogen-containing 5- or 6-membered heterocyclic ring having a double bond within the ring of the present invention include compounds having a heterocyclic ring such as triazole, pyridine, pyrimidine, pyrazole, piperazine, tetrazole, acridine, adenine, benzothiazole, triazine, thiadiazole, imidazole, benzimidazole, thiazoline, indoline or imidazoline.

Specific examples of this stabilizer of the present invention include 1,2,4-triazole, 3-amino-1,2,4-triazole (Compound 1), mercapto-1,2,4-triazole (Compound 2), 3-amino-5-carboxy-1,2,4-triazole, 2,6-dimethylolpyridine (Compound 3), 4-dimethylaminopyridine (Compound 4), mercaptopyrimidine (Compound 5), 2-aminonaphtho[1,2] thiazole, benzothiazole, 2-mercaptobenzothiazole (Compound 6), 2-aminobenzothiazole, 2-amino-1,3,4-thiadiazole (Compound 7), 2,5-dimercapto-1,3,4-thiadiazole, 5-amino-1,3,4-thiadiazole-2-thiol, 2,4,6-triamino-1,3,5-triazine (Compound 8), 1,3,5-triazine-2,4,6-trithiol, 3-mercapto-4-methyl-4H-1,2,4-triazole, 5-mercapto-1-methyltetrazole, 1-phenyl-5-mercapto-1H-tetrazole, 5-methyl-1,3,4-thiadiazole-2-thiol, mercaptothiazole, mercaptotetrazole, 2-mercaptobenzoxazole, 2-mercaptobenzothiazole sodium salt, furfurylmercaptan, mercaptoimidazole, 1-acetylimidazole, 2-mercapto-1-methylimidzole (Compound 9), N-methylimidazole (Compound 10), 1,2-dimethylimidazole, 2-aminobenzimidazole, 2-mercaptobenzimidazole (Compound 11), 2-mercaptothiazoline (Table 1: Compound 12), acridine, 1-(2-aminoethyl)piperazine, 5-amino-1H tetrazole, 3,5-dimethylpyrazole and phenothiazine.

Examples of the stabilizer comprising an amine represented by formula (2) include compounds where in formula (2), $R_5$, $R_6$ and $R_7$ each independently represents hydrogen, an alkyl group, an allyl group, an aryl group, an aralkyl group, an alkenyl group, an alkynyl group, an alicyclic group or a heterocyclic group, or two or three of $R_5$, $R_6$ and $R_7$ are combined to form a cyclic structure (provided that at least one of $R_5$, $R_6$ and $R_7$ is selected from those other than hydrogen).

More specifically, the alkyl group represented by $R_5$, $R_6$ or $R_7$ is a substituted or unsubstituted, linear or branched alkyl group having from 1 to 20 carbon atoms and examples thereof include a methyl group, an ethyl group, a propyl group, an isopropyl group, a butyl group, an isobutyl group, a sec-butyl group, a pentyl group, a hexyl group, a heptyl group, an octyl group, a 3-methoxypropyl group, a 4-chlorobutyl group and a 2-diethylaminoethyl group.

The allyl group is a substituted or unsubstituted allyl group and specific examples thereof include a 2-methylallyl group and a 3-chloroallyl group.

The aryl group is a substituted or unsubstituted aryl group and specific examples thereof include a phenyl group, a tolyl group, a xylyl group, a 4-ethylphenyl group, a 4-tertbutylphenyl group, a 4-methoxyphenyl group, a 4-diethylaminophenyl group, a 2-methylphenyl group, a 2-methoxyphenyl group, a naphthyl group and a 4-methylnaphthyl group.

The aralkyl group is a substituted or unsubstituted aralkyl group and specific examples thereof include a benzyl group, a phenethyl group, a propiophenyl group, an α-naphthylmethyl group, a β-naphthylmethyl group and p-methoxybenzyl group.

The alkenyl group is a substituted or unsubstituted alkenyl group preferably having from 2 to 12 carbon atoms and specific examples thereof include a vinyl group, a propenyl group, a butenyl group, a pentenyl group, a hexenyl group, a heptenyl group, an octenyl group, a dodecinyl group and a prenyl group.

The alkynyl group is a substituted or unsubstituted alkynyl group preferably having from 4 to 12 carbon atoms and specific examples thereof include a butynyl group, a pentynyl group, a hexynyl group and an octynyl group.

The alicyclic group is a substituted or unsubstituted alicyclic group and specific examples thereof include a cyclohexyl group, a 4-methylcyclohexyl group, a cyclopentyl group and a cycloheptyl group.

The heterocyclic group is a substituted or unsubstituted heterocyclic group and specific examples thereof include a pyridyl group, a quinolyl group, a methylpyridyl group, an indolyl group, an imidazolyl group and a triazyl group.

Specific examples of this stabilizer include hexylamine, di-n-butylamine (Compound 14), dipropylamine, triethylamine, diethyldiamine, N,N,N',N'-tetraethylmethylenediamine (Compound 15), 2-ethylaminoethanol, 3-diethylamino-1-propanol, tributylamine, aniline, naphthylamine, benzylamine, diallylamine, phenylenediamine, octenylamine, cyclohexylamine 3-aminopyridine, aminoimidazole, hexamethylenetetramine, N-methylmorpholine (Compound 13) and triethylenediamine (Compound 16).

The stabilizer comprising a thiol represented by formula (3) of the present invention a compound where an alkyl group, an aryl group, an aralkyl group, an alkenyl group, an alkynyl group, an alicyclic group or a heterocyclic group is bonded with a thiol group or a sodium salt thereof and examples thereof include the compounds where in formula (3), $R_8$ is an alkyl group, an allyl group, an aralkyl group, an alkenyl group, an alicyclic group or a heterocyclic group, and X is sodium or hydrogen.

More specifically, the alkyl group is a substituted or unsubstituted, linear or branched alkyl group having from 1 to 20 carbon atoms and examples thereof include a methyl group, an ethyl group, a propyl group, an isopropyl group, a butyl group, an isobutyl group, a sec-butyl group, a pentyl group, a hexyl group, a heptyl group, an octyl group, a 3-methoxypropyl group, a 4-chlorobutyl group and a 2-diethylaminoethyl group.

The aryl group is a substituted or unsubstituted aryl group and specific examples thereof include a phenyl group, a tolyl group, a xylyl group, a 4-ethylphenyl group, a 4-tertbutylphenyl group, a 4-methoxyphenyl group, a 4-diethylaminophenyl group, a 2-methylphenyl group, a 2-methoxyphenyl group, a naphthyl group and a 4-methylnaphthyl group.

The aralkyl group is a substituted or unsubstituted aralkyl group and specific examples thereof include a benzyl group, a phenethyl group, a propiophenyl group, an α-naphthylmethyl group, a β-naphthylmethyl group and a p-methoxybenzyl group.

The alkenyl group is a substituted or unsubstituted alkenyl group preferably having from 2 to 12 carbon atoms and specific examples thereof include a vinyl group, a propenyl group, a butenyl group, a pentenyl group, a hexenyl group, a heptenyl group, an octenyl group, a dodecinyl group and a prenyl group.

The alkynyl group is a substituted or unsubstituted alkynyl group preferably having from 4 to 12 carbon atoms and specific examples thereof include a butynyl group, a pentynyl group, a hexynyl group and an octynyl group.

The alicyclic group is a substituted or unsubstituted alicyclic group and specific examples thereof include a cyclohexyl group, a 4-methylcyclohexyl group, a cyclopentyl group and a cycloheptyl group.

The heterocyclic group is a substituted or unsubstituted heterocyclic group and specific examples thereof include a pyridyl group, a quinolyl group, a methyl-pyridyl group, an indolyl group, an imidazolyl group and a triazyl group.

Specific examples of this stabilizer include propanethiol, octanethiol, decanethiol (Compound 17), dodecanethiol (Compound 18), benzenethiol, toluenethiol, naphthalenethiol, mercaptoethanol, ethyl-2-mercaptoacetate, cyclopentanethiol, 2-benzimidazolethiol and 1,2,4-triazol-3-thiol.

Among the above-described stabilizers, heterocyclic compounds containing a tertiary nitrogen atom within the ring are particularly effective for the thermal stabilization.

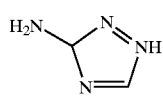

(Compound 1)

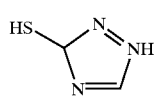

(Compound 2)

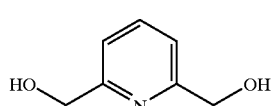

(Compound 3)

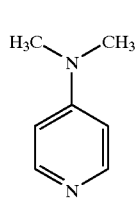

(Compound 4)

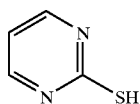

(Compound 5)

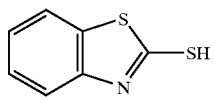

(Compound 6)

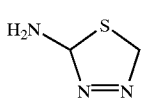

(Compound 7)

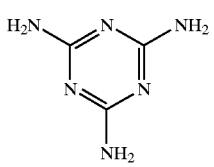

(Compound 8)

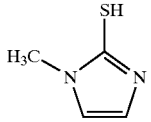

(Compound 9)

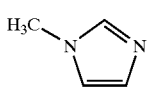

(Compound 10)

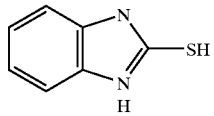

(Compound 11)

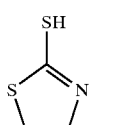

(Compound 12)

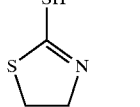

(Compound 13)

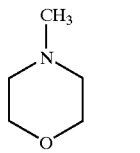

(Compound 14)

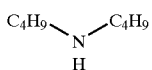

(Compound 15)

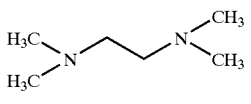

(Compound 16)

CH$_3$(CH$_2$)$_9$SH (Compound 17)

CH$_3$(CH$_2$)$_{11}$SH (Compound 18)

Specific examples of the anion moiety in the organic borate salt represented by formula (1) for use in the present invention include n-butyltriphenyl borate, n-octyltriphenyl borate, n-dodecyltriphenyl borate, sec-butyltriphenyl borate, tert-butyltriphenyl borate, benzyltriphenyl borate, n-butyltrianisyl borate, ethyltributyl borate, phenethyltrimethyl borate, phenyltruisobutyl borate, n-pentyltri (4methoxyphenyl) borate, n-butyltri (6-methoxy-2-naphthyl) borate, methyltri (1-naphthyl) borate, n-butyltrinaphthyl borate, n-butyltri (4-methylnaphthyl) borate and ethyltriacenaphthyl borate.

Specific examples of the cation moiety in the organic borate salt represented by formula (1) for use in the present invention include tetramethylammonium, tetraethylammonium, tetra-n-butylammonium, tetra-n-octylammonium, methylquinolinium, methylpyridinium, tetramethylphosphonium, tetra-n-butylphosphonium, trimethylsulfonium, triphenylsulfonium, trimethyloxosulfonium, diphenyliodonium, di(4-tert-butylphenyl) iodonium, (2-hydroxyethyl)trimethylammonium, lithium, potassium, sodium, cyanine dye cation, azomethine dye cation, xanthene dye cation and leuco dye cation.

Organic borate salts consist of the above-described anion moiety and cation moiety may be used in the present invention, however, the present invention is by no means limited thereto.

In the present invention, the method for adding the stabilizer of the present invention to the organic borate salt represented by formula (1) is not particularly limited, however, the stabilizer of the present invention is preferably dissolved in a solvent in which the organic borate salt is dissolved, because stability against heat and aging can be obtained. When these are dissolved under heating at a temperature of from room temperature to the boiling point of the solvent or a temperature lower than the melting point or decomposition point of the organic borate salt itself, whichever is lower, the organic borate salt is prevented from the decomposition and higher stability against heat and aging can be obtained as compared with the case where the stabilizer of the present invention is not added.

The stabilizer of the present invention is considered to exert the stabilizing effect based on the interaction or the like during the thermal reaction of the organic borate salt represented by formula (1). This is also inferred from the fact that a sufficiently high effect is brought out even when the amount of the stabilizer of the present invention added is very small on the basis of the organic borate salt and the effect is higher than the effect attained only by mere neutralization of the acidic substance within the system.

The stabilizer of the present invention also has a property of not inhibiting useful reaction intended, such as photoreaction, even when it is added in an excess amount.

By adding the stabilizer of the present invention, the organic borate salt can have heat stability. The organic borate salt is imparted with heat stability and aging stability in the process where the mixture of a composition having added thereto the stabilizer of the present invention is applied continuously or using, if desired, one or more means of dissolution, dispersion, kneading, emulsification and the like to a medium or solvent.

As described above, the stabilizer of the present invention is effective as a stabilizer of an organic borate salt and by combining it with an organic borate salt, the resulting composition can be used as a photosensitive composition.

The ratio of the stabilizer of the present invention to the organic borate salt used may be freely selected, however, the stabilizer is preferably used in an amount of from 10 to 500 wt %, more preferably from 50 to 200 wt %, based on the organic borate salt. Two or more stabilizers and two or more organic borate salts may be used.

The organic borate salt is usually accelerated to decompose by heat if a sensitizing dye is present, however, in the composition comprising an organic borate salt having added thereto the stabilizer of the present invention, the organic borate salt is prevented from the thermal decomposition or reaction even when a sensitizing dye having light absorbing power is added to the composition. Accordingly, change or decomposition of the sensitizing dye due to the reaction between the sensitizing dye and the organic borate salt is difficult to occur as compared with the case where the stabilizer of the present invention is absent.

The term "sensitizing dye" as used in the present invention means a cationic dye such as cyanine, xanthene, oxazine, thiazine, diarylmethane, triarylmethane and pyrylium, or an electrically neutral dye, namely, an organic dye not comprising a counter ion but containing +∘− due to resonance within the same molecule, such as merocyanine, coumarin, indigo, aromatic amine, phthalocyanine, azo and quinone-type sensitizing dyes.

In the case of a cationic dye, the counter anion may be any anion, for example, a halogen anion such as chloride, bromide or iodide anion, a benzenesulfonate anion, a p-toluenesulfonate anion, a methanesulfonate anion, an organic borate anion, a $BF_4$ anion, a $PF_6$ anion or a perchlorate anion.

Specific examples of the cationic dye as the sensitizing dye include Crystal Violet (CI42555), Methyl Violet (CI42535), Malachite Green (CI42000), Fuchsin (CI42510), Crystal Violet-Carbinol Base (CI42555:1), Parafuchsin (CI42500), Rhodamine B (CI45170), Victoria Blue B (CI44045), Victoria Pure Blue BOH (CI42595), Brilliant Green (CI42040), Night Blue BX (CI51185), Neutral Red (CI50040), Basic Orange 21 (CI48035), Basic Yellow 11, Basic Yellow 21, Basic Yellow 22, Basic Red 1 (CI45160), Basic Red 5 (CI50040), Basic Red 13 (CI48015), Basic Violet 7 (CI48020), Basic Violet 11 (CI45175), p-toluenesulfonate or naphthalenesulfonate of Crystal Violet, p-toluenesulfonate or perchlorate of Victoria Blue B, p-toluenesulfonate or $BF_4$ salt of Basic Orange 21, and naphthalenesulfonate or $PF_6$ salt of Basic Red 5.

Specific examples of the electrically neutral dye include 3-allyl-1-carboxymethyl-5-[2-(3-ethyl-2(3H)benzoxazolylidene]-2-thiohydantoin, 4-[2-(3-ethyl-2(3H)benzothiazolylidene)ethylidene]-3-phenyl-2-isooxazolin-5-one, 3-(2-benzothiazolyl)-7-(diethylamino)coumarin, 3-(2-benzimidazolyl)-7-(diethylamino)coumarin, ethyl 2,3,6,7-tetrahydro-11-oxo-1H,5H,11H-[1]benzopyrano[6,7,8-ij]quinalizine-10-carboxylate, N,N'-diethylindigo, thioxoindigo, 2-dimethyl-aminoanthraquinone, 4-hydroxyazobenzene and 4-phenylamino-4'-nitroazobenzne.

The sensitizing dye which can be freely combined with an organic borate salt and the stabilizer to obtain a photosensitive composition is added in an amount of from 1 to 100 wt %, preferably from 5 to 30 wt %, based on the photosensitive composition. If the concentration of the sensitizing dye is less than the this range, absorption of light is reduced and the light energy cannot be used efficiently, whereas if the concentration greatly exceeds the above-described range, light is excessively absorbed by the dye, as a result, the light intensity extremely decreases in the area farther from the surface irradiated by light and sufficiently high photosensitivity cannot be ensured in the depth. The photosensitive composition of the present invention can exhibit efficient photoreaction even when two or more of the above-described sensitizing dyes are present together and due to the action of the stabilizer of the present invention, the composition can have stability.

The stabilizer of the present invention exerts the effect of preventing the thermal decomposition or reaction of an organic borate salt even in a composition comprising the stabilizer of the present invention and an organic borate salt or in a polymerizable composition obtained by adding at least one compound having one or more addition-polymerizable ethylenically unsaturated bond to a composition containing the stabilizer of the present invention, an organic borate salt and a sensitizing dye.

In the state where the stabilizer is absent, the organic borate salt thermally decomposes or reacts, the active species generated causes chain reaction of the double bonds of the compound having an ethylenically unsaturated bond, and unintended addition polymerization may proceed. However, in the polymerizable composition containing the stabilizer of the present invention, the organic borate salt is prevented from the thermal decomposition or reaction and thereby unintended thermal polymerization reaction during the storage is inhibited, hence, the composition can have aging stability.

A photosensitive composition can be obtained from a compound having one or two nitrogen-containing heterocyclic ring having a double bond within the ring or a compound having a thiol group represented by formula (3), out of the stabilizers of the present invention, and an organic borate salt represented by formula (1). This photosensitive composition may further contain the above-described sensitizing dye. These photosensitive compositions can efficiently initiate photopolymerization even in the presence of oxygen.

The bisimidazole compound for use in the present invention is a compound having a group resulting from two imidazole rings being combined at any site and specific examples thereof include 2,2'-bis(4,5'-dimethylimidazole) and 2,2'-bis(o-chlorophenyl)-4,4',5,5'-tetraphenyl-1,2'-biimidazole. The compound selected from the stabilizers which can be used in the photosensitive composition, and the organic borate salt are preferably used in an amount of from 10 to 200 wt %, more preferably from 20 to 100 wt %, based on the photosensitive composition obtained by the optional combination thereof.

The monomer having one or more ethylenically unsaturated bond for use in the present invention includes a (meth) acrylic acid and an ester thereof and examples thereof include methyl (meth)acrylate, butyl (meth)acrylate, benzyl (meth)acrylate, phenethyl (meth)acrylate, isobornyl (meth) acrylate, cyclohexyl (meth)acrylate, 2-hydoxyethyl (meth) acrylate, 2-hydroxypropyl (meth)acrylate, 2-hydroxy-3-phenoxypropyl (meth)acrylate, N,N-dimethylaminoethyl (meth)acrylate, glycidyl (meth)acrylate and methacryloyloxyethyl isocyanate. A (meth)acrylamide and an N-substitution product thereof, such as N-methyl(meth)acrylamide, N,N-diethyl(meth)acrylamide, N-butoxymethylacrylamide, isobutoxymethylacrylamide, and (meth)acrylamide-2-methylpropanesulfonic acid and a sodium salt thereof, may also be used.

Other examples of the monomer having one or more ethylenically unsaturated bond for use in the present invention include compounds having an N-vinylamide structure such as N-vinylacetamide, N-vinylpropionamide and N-vinyl-butanamide; polyhydric alcohol (meth)acrylates which is an ester obtained by the esterification of an unsaturated carboxylic acid or a polycarboxylic acid with a polyhydric compound, such as phenoxydiethoxy (meth) acrylate, polyethylene glycol di(meth)acrylate, 1,3-butanediol di(meth)acrylate, neopentyl glycol di(meth) acrylate, 2,2-bis[4-(meth)acryloyloxypolyethoxyphenyl] propane, hydroxypivalic acid neopentyl glycol di(meth) acrylate, glycerin di(meth)acrylate, glycerin tri(meth) acrylate, trimethylolethane di(meth) acrylate, triethylolpropane di(meth)acrylate, trimethylolpropane tri (meth)acrylate, isocyanuric acid trierythritol tri(meth) acrylate, pentaerythritol di(meth) acrylate, pentaerythritol tri(meth) acrylate, pentaerythritol tetra(meth)acrylate, dipentaerythritol tri(meth)acrylate, dipentaerythritol tetra (meth)acrylate, dipentaerythritol penta(meth)acrylate, dipentaerythritol hexa(meth)acrylate, and compounds represented by formulae (4) and (5) where n=1 to 9; epoxy (meth)acrylates; and urethane (meth)acrylates obtained by the reaction with (meth)acryloyloxy isocyanate.

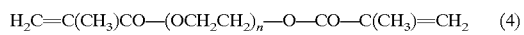

$$H_2C=C(CH_3)CO-(OCH_2CH_2)_n-O-CO-C(CH_3)=CH_2 \quad (4)$$

(wherein n is an integer of from 1 to 9);

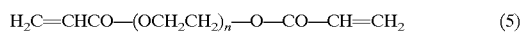

$$H_2C=CHCO-(OCH_2CH_2)_n-O-CO-CH=CH_2 \quad (5)$$

(wherein n is an integer of from 1 to 9).

The term "(meth)acryl" as used herein means "methacryl" and "acryl".

The compound having an ethylenically unsaturated bond for use in a polymerizable composition comprising any combination of an organic borate salt and the stabilizer is added in an amount of from 1 to 5,000 parts by weight, preferably from 30 to 2,000 parts by weight, per 1 part by weight of the photosensitive composition. Even when two or more of the compound having one or more ethylenically unsaturated bond are added, the stabilizer of the present invention exerts the effect to increase the heat stability and in turn, the polymerizable composition exhibits high sensitivity even in the presence of oxygen. Furthermore, the stabilizer can be used in a composition containing an organic borate salt, other than the polymerizable composition of the present invention.

The high molecular polymer for use in the present invention is described below. The high molecular polymer is preferably a linear polymer containing one or more monomer selected from (meth)acrylic acid, (meth)acrylic ester, N-vinylamide, (meth)acrylamide, N-substituted (meth) acrylamide, N-disubstituted (meth)acrylamide, styrene, alkyl-substituted styrene, chloromethylstyrene, vinylphenol and alkyl-substituted vinylphenol, and having a molecular weight of from 1,000 to 500,000, preferably from 5,000 to 100,000. By adjusting the acid value of this high molecular polymer to be 5 mgKOH/g or less, a high molecular polymer insoluble in an alkaline aqueous solution can be obtained. On the other hand, by adjusting the acid value to be from 20 to 800 mgKOH/g, preferably from 30 to 500 mgKOH/g, a high molecular polymer soluble in an alkaline aqueous solution can be obtained.

In the case when the polymerizable composition is used as a resist, the high molecular polymer for use in the present invention is necessary to dissolve in a solvent at the development and preferably comprises a monomer having only one polymerizable group. Examples of the monomer used herein include (meth)acrylic acid, methyl (meth)acrylate, butyl (meth)acrylate, benzyl (meth)acrylate, phenethyl (meth)acrylate, isobornyl (meth)acrylate, cyclohexyl (meth)

acrylate, 2-hydroxyethyl (meth)acrylate, 2-hydroxypropyl (meth)acrylate, 2-hydroxy-3-phenoxypropyl (meth)acrylate, N,N-dimethylaminoethyl (meth)acrylate, glycidyl (meth) acrylate, methacryloyloxyethyl isocyanate, N-vinylacetamide, (meth)acrylamide, N-methyl(meth) acrylamide, N,N-diethyl(meth)acrylamide, n-butoxymethylacrylamide, isobutoxymethylacrylamide, N-hydroxymethylacrylamide, (meth)acrylamido-2-methylpropanesulfonic acid, N-vinylpyrrolidone, styrene, α-methylstyrene, p-chloromethylstyrene and p-vinylphenol.

The high molecular polymer of the present invention preferably comprises a copolymer of a (meth)acrylic acid and a (meth)acrylic ester as a main component. Examples thereof include a methacrylic acid-butyl methacrylate copolymer, a methacrylic acid-benzyl methacrylate copolymer, an acrylic acid-methyl methacrylate-butyl methacrylate copolymer, a methacrylic acid-butyl methacrylate-isobornyl methacrylate copolymer, a methacrylic acid-2-hydroxyethyl methacrylate-butyl methacrylate copolymer, a methacrylic acid-methyl methacrylate-butyl methacrylate-2-hydroxyethyl acrylate-styrene copolymer, a methacrylic acid-butyl methacrylate-glycidyl methacrylate copolymer, a methacrylic acid-butyl methacrylate-cyclohexyl methacrylate-styrene copolymer, a methacrylic acid-butyl methacrylate-styrene copolymer and a methacrylic acid-acrylic acid-methyl methacrylate-butyl methacrylate copolymer. The composition and the compositional ratio of these copolymers are not particularly limited and copolymers and copolymer mixtures obtained by any combination at any compositional ratio may be used. The high molecular polymer is added in an amount of from 0.5 to 200 parts by weight, preferably from 1 to 100 parts by weight, based on the photosensitive composition comprising any combination of an organic borate salt and the stabilizer.

Examples of the pigment for use in the present invention include, in term of the color index number, C.I. Pigment Yellow 12, 13, 14, 17, 20, 24, 55, 83, 86, 93, 109, 110, 117, 125, 137, 139, 147, 148, 153, 154, 166 and 168, C.I. Pigment Orange 36, 43, 51, 55, 59 and 61, C.I. Pigment Red 9, 97, 122, 123, 149, 168, 177, 180, 192, 215, 216, 217, 220, 223, 224, 226, 227, 228 and 240, C.I. Pigment Violet 19, 23, 29, 30, 37, 40 and 50, C.I. Pigment Blue 15, 15:1, 15:4, 15:6, 22, 60 and 64, C.I. Pigment Green 7 and 36, C.I. Pigment Brown 23, 25 and 26, and C.I. Pigment Black 7, and further include carbon black, surface resin treated carbon black, titanium black, aniline black, titanium white, talc, alumina and iron oxide.

The pigment may be dispersed in the polymerizable composition using, if desired, an appropriate dispersant. The pigment is used in an amount of from 0.05 to 80 parts by weight, preferably from 1 to 50 parts by weight, based on the polymerizable composition obtained by adding a monomer having one or more ethylenically unsaturated bond to a photosensitive composition comprising any combination of a compound having one or more nitrogen-containing 5- or 6-membered heterocyclic ring having a double bond within the ring or a compound having a thiol group represented by formula (3), out of the stabilizers of the present invention, and an organic borate salt represented by formula (1). Two or more of these compounds may be used in combination to attain proper tone and light-shielding ratio and even in this case, the polymerizable composition of the present invention exhibits high sensitivity.

The polymerizable composition obtained by adding a compound having one or more ethylenically unsaturated bond to the photosensitive composition comprising an organic borate salt, the stabilizer and a sensitizing dye, the polymerizable composition further containing a high molecular polymer, and the polymerizable composition still further containing a pigment each may use a solvent according to the use end.

Examples of the solvent include cyclohexane, isophorone, diethylene glycol dimethyl ether, ethylene glycol diethyl ether, tetrahydrofuran, xylene, ethylbenzene, ethyl cellosolve, butyl cellosolve, methyl cellosolve acetate, ethyl cellosolve acetate, acetone, cyclohexanone, methyl ethyl ketone, methyl isobutyl ketone, methyl-n-amyl ketone, diethylene glycol monomethyl ether, diethylene glycol monoethyl ether, diethylene glycol dimethyl ether, propylene glycol monomethyl ether acetate, ethyl acetate, isoamyl acetate, ethyl lactate and dichloroethane. These solvents may be used individually or in combination of two or more thereof. The solvent is added in an amount of from 0.05 to 100 parts by weight based on the polymerizable composition. The solvent is preferably removed by evaporation in advance of the polymerization.

The polymerizable composition is coated on a substrate, the solvent is evaporated, and the resist film obtained is irradiated with light through a pattern mask. As a result, the photosensitive composition exposed to light is activated to generate radicals and thereby the ethylenically unsaturated bonds cause chain reaction to connect with each other, thus, the polymerization proceeds. The polymerization does not proceed in the area not exposed to light and by removing the area using an excess of an appropriate solvent such as methyl alcohol, ethyl alcohol, isopropyl alcohol, cyclohexane, isophorone, cellosolve acetate, diethylene glycol dimethyl ether, ethylene glycol diethyl ether, xylene, ethylbenzene, ethyl cellosolve, butyl cellosolve, acetone, cyclohexanone, methyl ethyl ketone, methyl isobutyl ketone, methyl-n-amyl ketone, propylene glycol monomethyl ether acetate, ethyl acetate, isoamyl acetate, ethyl lactate or dichloromethane, the area exposed to light remains on the substrate and a colored pattern in accordance with the pigment added can be formed.

At this time, when the high molecular polymer contained in the polymerizable composition has a high acid value (20 to 800 mgKOH/g), the unexposed area can be removed using the above-described organic solvent and additionally an alkaline aqueous solution (pH=9 to 12). The alkaline aqueous solution which can be used is an aqueous solution containing one or more of sodium hydroxide, potassium hydroxide, sodium carbonate, potassium carbonate and tri-alkylamine.

In this case, the photosensitive composition comprising a compound having one or more nitrogen-containing 5- or 6-membered heterocyclic ring having a double bond within the ring or a compound having a thiol group represented by formula (3) and an organic borate salt represented by formula (1) of the present invention has good photopolymerization initiating ability even in the presence of oxygen and accordingly, irrespective of the presence or absence of an oxygen-blocking overcoat on the film of the polymerizable composition coated on a substrate, the same colored pattern can be formed.

The present invention is described in greater detail below by referring to the Examples and Comparative Examples, however, the present invention should not be construed as being limited thereto as long as the scope of the present invention is persisted.

The quantitative determination of the organic borate salt was performed using a high performance liquid chromatography (HPLC) (column: SHODEX C8-5B; mobile phase: a 85:15 mixture of acetonitrile containing 4 mM of tetraoctylammoniurm bromide:water; detector: SPD-10AV, manufactured by Shimadzu Seisakusho).

The effect of the stabilizers of the present invention was verified by Examples 1 to 8 and Comparative Examples 1 to 5.

EXAMPLE 1

A composition was prepared by dissolving 0.1 part by weight of mercaptobenzothiazole as the stabilizer of the present invention and 3 parts by weight of tetrabutylammonium n-butyltri(4-methylnaphthyl) borate as the organic borate salt in 100 parts by weight of γ-butyrolactone. The composition obtained was kept at 90° C. for 5 hours and then, the residual ratio of the organic borate salt was 98%.

EXAMPLE 2

A composition was prepared by dissolving 0.1 part by weight of 3-amino-1,2,4-triazole as the stabilizer of the present invention and 3 parts by weight of tetrabutylammonium n-butyltrinaphthyl borate as the organic borate salt in 100 parts by weight of γ-butyrolactone. The composition obtained was kept at 90° C. for 5 hours and then, the residual ratio of the organic borate salt was 99%.

EXAMPLE 3

A composition was prepared by dissolving 0.2 part by weight of 2,4,6-triamino-1,3,5-triazine as the stabilizer of the present invention and 3 parts by weight of 1,1,5,5-tetrakis(p-diethylaminophenyl)-2,4-pentadienilium n-butyltriphenyl borate as the organic borate salt in 100 parts by weight of γ-butyrolactone. The composition obtained was kept at 90° C. for 5 hours and then, the residual ratio of the organic borate salt was 90%.

EXAMPLE 4

A photosensitive composition of the present invention was prepared by dissolving 0.1 part by weight of N,N,N',N'-tetramethylethylenediamine as the stabilizer of the present invention, 3 parts by weight of tetrabutylammonium n-butyltri(p-ethoxyphenyl) borate as the organic borate salt, and 0.5 part by weight of Crystal Violet as the sensitizing dye in 100 parts by weight of γ-butyrolactone. The composition obtained was kept at 90° C. for 5 hours and then, the residual ratio of the organic borate salt was 82%.

EXAMPLE 5

A polymerizable composition of the present invention was prepared by adding 100 parts by weight of epoxy acrylate having an acidity of 70 (mgKOH/g), 2 parts by weight of tetrabutylammonium n-butyltrinaphthyl borate and 0.15 part by weight of mercaptobenzimidazole as the stabilizer of the present invention to 100 parts by weight of ethyl acetate. The composition obtained was stored at 55° C. for 48 hours and then, the residual ratio of the organic borate salt was measured and found to be 72%.

EXAMPLE 6

A polymerizable composition of the present invention was prepared by adding 100 parts by weight of epoxy acrylate having an acidity of 70 (mgKOH/g), 2 parts by weight of tetrabutylammonium butyltri(4-methylnaphthyl) borate and 0.15 part by weight of dimercaptothiadiazole as the stabilizer of the present invention to 100 parts by weight of ethyl acetate. The composition obtained was stored at 55° C. for 48 hours and then, the residual ratio of the organic borate salt was 86%.

EXAMPLE 7

A polymerizable composition of the present invention was prepared by mixing 100 parts by weight of propylene glycol monomethyl acetate, 100 parts by weight of an acrylate monomer having an acidity of 60 (mgKOH/g), 2 parts by weight of tetrabutylammonium butyltrinaphthyl borate, 1 part by weight of Basic Red 1 and 0.5 part by weight of 2,6dimethylolpyridine as the stabilizer of the present invention.

For determining the sensitivity of the polymerizable composition prepared, the polymerizable composition was coated on a polyethylene terephthalate film to have a dry thickness of 5 μm under the condition of shielding light., and then the solvent was evaporated at room temperature. The exposure amount necessary for polymerizing and curing the polymerizable composition of the present invention was measured using a Deep UV lamp as the light source and the energy obtained was used as the index for the sensitivity (the smaller the value, the higher the sensitivity). The polymerizable composition prepared above had sensitivity of 5.6 mJ/cm$^2$. This polymerizable composition was stored in a dark place at 80° C. for 3 hours and then, the residual ratio of tetrabutylammonium butyltrinaphthyl borate as the organic borate salt was 95%. The sensitivity determined in the same manner as above was 5.6 mJ/cm$^2$.

EXAMPLE 8

A polymerizable composition of the present invention was prepared by mixing 100 parts by weight of methylene chloride, 100 parts by weight of pentaerythritol tetraacrylate, 100 parts by weight of an epoxy acrylate having an acidity of 70 (mgKOH/g)f 1 part by weight of tetrabutylammonium butyltri(6-methoxy-β-naphthyl) borate, 1 part by weight of Victoria Pure Blue BOH and 2 parts by weight of mercaptopyrimidine as the stabilizer of the present invention.

The sensitivity of the polymerizable composition prepared was determined in the same manner as in Example 7 and found to be 5.6 mJ/cm$^2$. This polymerizable composition was stored in a dark place at 80° C. for 3 hours and then, the residual ratio of tetrabutylammonium butyltri(6-methoxy-β-naphthyl) borate as the organic borate salt was 98%. The sensitivity determined in the same manner as above was 5.6 mJ/cm$^2$.

COMPARATIVE EXAMPLE 1

A composition prepared in the same manner as in Example 1 except for excluding the stabilizer of the composition was evaluated in the same manner as in Example 1. After the storage at 90° C. for 5 hours, the residual ratio of tetrabutylammonium n-butyltri(4-methylnaphthyl) borate was 45%.

COMPARATIVE EXAMPLE 2

A composition prepared in the same manner as in Example 2 except for excluding the stabilizer of the composition was stored at 90° C. for 5 hours. Then, the residual ratio of tetrabutylammonium n-butyltrinaphthyl borate was 55%.

COMPARATIVE EXAMPLE 3

A composition prepared in the same manner as in Example 3 except for excluding the stabilizer of the composition was stored at 90° C. for 5 hours. Then, the residual ratio of 1,1,5,5-tetrakis(p-diethylaminophenyl)-2,4-pentadienilium n-butyltriphenyl borate was 50%.

COMPARATIVE EXAMPLE 4

A composition prepared in the same manner as in Example 4 except for excluding the stabilizer of the composition was stored at 90° C. for 5 hours. Then, the residual ratio of tetrabutylammonium n-butyltri(p-ethoxyphenyl) borate was 55%.

COMPARATIVE EXAMPLE 5

A polymerizable composition was prepared in the same manner as in Example 7 except for excluding the stabilizer of the polymerizable composition. The sensitivity of the polymerizable composition immediately after the preparation was determined in the same manner as in Example 7 and then, the exposure amount necessary for curing the composition was 5.6 mJ/cm². After storage at 80° C. for 3 hours, the residual ratio of tetrabutylammonium butyltrinaphthyl borate was 50% and the sensitivity was 56.2 mJ/cm².

It is apparent from the comparison between Example 1 and Comparative Example 1, Example 2 and Comparative Example 2, Example 3 and Comparative Example 3, and Example 4 and Comparative Example 4, respectively, that the organic borate salt is prevented from thermal decomposition by the stabilizer of the present invention. Furthermore, as is apparent from the comparison between Example 7 and Comparative Example 5, the decomposition is prevented while maintaining the sensitivity during the storage by the stabilizer of the present invention.

The effect of the presence or absence of oxygen on the photocurability of the polymerizable composition of the present invention is described by referring to Examples 9, 10, 14 and 15 and Comparative Example 6. In these Examples, the polymerizable composition prepared is called a resist for the sake of convenience. In these Examples, an alkali development-type black resist was formed by the production method of a black matrix for color liquid crystal displays, particularly by the commonly employed pigment dispersion method in which photopolymerization of a thin film in the presence of oxygen is required in view of simplification of the process.

A synthesis example of a high molecular polymer soluble in an alkaline aqueous solution, which is a high molecular polymer used in these Examples, is described below. In the following, unless otherwise indicated, the "part" is "part by weight".

Synthesis Example of High Molecular Polymer

A mixed solution containing 350 parts of cyclohexanone, 26.2 parts of styrene, 23.3 parts of 2-hydroxyethyl acrylate, 35 parts of methacrylic acid, 20.5 parts of methyl methacrylate and 70 parts of butyl methacrylate was heated at 90° C. and reacted for 3 hours while gradually adding dropwise thereto a dissolution product of 290 parts of cyclohexanone, 26.2 parts of styrene, 23.3 parts of 2-hydroxyethyl acrylate, 35 parts of methacrylic acid, 20.5 parts of methyl methacrylate, 70 parts of butyl methacrylate and 1.75 parts of azobisisobutyronitrile. Thereto, 10 parts of cyclohexanone having dissolved therein 0.70 part of azobisisobutyronitrile was added and the mixed solution was reacted for another one hour. A part of the resulting high molecular polymer solution was dried by heating in vacuum at 90° C. for 60 minutes and the non-volatilized content measured. The non-volatile content was adjusted to 25% by adding cyclohexanone to obtain a high molecular polymer solution. This polymer had an average molecular weight of about 50,000 and an acid value of 120 mgKOH/g.

Preparation of Black Resist

| | |
|---|---|
| High molecular polymer solution | 34 parts |
| Carbon black | 8.0 parts |
| (FW200, produced by Degssa KK) | |
| Dispersant (HOMOGENOL L-18, | 0.8 part |
| produced by Kao Corporation) | |
| Cyclohexanone | 29 parts |

These components were mixed, dispersed in a bead mill for 360 minutes and filtered through a 0.7-μm filter to prepare a black pigment dispersion solution. Thereafter, the following components were thoroughly mixed in a container.

| | |
|---|---|
| Black pigment dispersion solution | 56 parts |
| Trimethylolpropane triacrylate | 4.15 parts |
| Compound A | 1.00 part |
| Compound B | 0.20 part |
| Compound C | 1.00 part |
| Cyclohexanone | 37.3 parts |

The resulting mixed solution was filtered through a 1.0-μm filter to prepare Black Resist 1 having a non-volatile content of about 20%.

In the Examples, a tetraalkylammonium organic borate salt as Compound A, a sensitizing dye as Compound B and an organic compound containing thiol as Compound C were combined as follows.

EXAMPLE 9

Compound A: tetrabutylammonium butyltrinaphthyl borate
Compound B: 3-Carboethoxy-7-(diethylamino) coumarin
Compound C: 2-mercaptobenzoxazole

EXAMPLE 10

Compound A: tetrabutylammonium methyltrinaphthyl borate
Compound B: Basic Yellow 21
Compound C: mercaptobenzothiazole
Bisimidazole Compound:
2,2'-bis(o-chlorophenyl)-4,4',5,5'-tetraphenyl-1,2'-bilmidazole

EXAMPLE 11

Compound A: tetrabutylammonium butyltri(4-tert-butylphenyl) borate
Compound B: Basic Yellow 21
Compound C: 2-mercaptothiazoline

EXAMPLE 12

Compound A: tetrabutylammonium butyltri(4-methylnaphthyl) borate
Compound B: Basic Yellow 13
Compound C: 5-methyl-1,3,4-thiadiazole-2-thiol

EXAMPLE 13

Compound A: tetrabutylammonium methyltri(4-methylnaphthyl) borate
Compound B: Basic Yellow 21
Compound C: 3-mercapto-4-methyl-4H-1,2,4-triazole Each resist solution was spin-coated on a clean glass plate having a thickness of 1 mm and a size of 10 cm×10 cm and dried at room temperature for 30 minutes and then at 700° for 20 minutes to form a 2 μm-thick resist film. The glass plate having coated thereon the resist film was designated as Glass Plate (A). For determining the spectral sensitivity, Glass Plate (A) was set in an irradiation spectroscope (Model JASCO CT-25CP, manufactured by Nippon Bunko KK) and exposed. The light source used was a 150W xenon lamp. After the exposure, the resist film was developed, thoroughly washed with water and dried to obtain a spectral image. The maximum step number where the resist film was not dissolved by the development with i-ray (365 nm), h-ray (405 nm) or g-ray (436 nm) in respective Examples, is shown in Table 1. The larger the step number, the higher the sensitivity.

EXAMPLE 14

The resist obtained in Example 9 was coated on a glass substrate in the same manner and dried at room temperature for 30 minutes and then at 70° C. for 20 minutes. On the resist coating formed, a 5% aqueous solution of polyvinyl alcohol (polymerization degree: about 1,000, saponification degree: about 98%) was coated by a spin coater to have a dry thickness of from 1.2 to 1.3 μm and dried at 70° C. for 20 minutes in a hot air oven to form an oxygen-blocking film. Thereafter, the spectral sensitivity was measured in the same manner as in Example 9.

COMPARATIVE EXAMPLE 6

A resist was prepared in the same manner as in Example 9 except that mercaptobenzoxazole used as Compound C in the resist composition of Example 9 was not added. The resist obtained was coated and dried on a glass substrate in the same manner as in Example 9 to prepare a resist film. The resist film formed was measured on the spectral sensitivity in the same manner as in Example 9.

EXAMPLE 15

A resist film with an oxygen-blocking film was formed on a glass substrate using the resist obtained in Example 10 in the same manner as in Example 14 and the spectral sensitivity thereof was measured in the same manner as in Example 9.

TABLE 1

|  | Spectral Sensitivity | | |
| --- | --- | --- | --- |
|  | g | h | i |
| Example 9 | 4 | 6 | 6 |
| Example 10 | 9 | 9 | 6 |
| Example 11 | 6 | 6 | 4 |
| Example 12 | 8 | 7 | 6 |
| Example 13 | 11 | 11 | 8 |
| Example 14 | 4 | 6 | 6 |
| Comparative Example 6 | 2 | 3 | 3 |
| Example 15 | 9 | 9 | 6 |

As apparent from the results in Table 1, comparison between Example 9 and Comparative Example 6 reveals that the sensitivity lowers when the organic compound having a thiol group according to the present invention is not added, comparison between Example 9 and Example 14 reveals that sensitivity equal to that in the case of an oxygen-blocking film being formed is obtained by adding the organic compound having a thiol group, and comparison between Example 10 and Example 15 reveals that the sensitivity is not lowered as compared with the case of an oxygen-blocking film being formed and hence, the polymerizable composition of the present invention exhibits high sensitivity even in the presence of oxygen.

By adding the stabilizer of the present invention to an organic borate salt, the organic borate salt can be remarkably improved in the heat stability and aging stability.

Also in the photosensitive composition of the present invention comprising the stabilizer of the present invention, an organic borate salt and a sensitizing dye, the organic borate salt can be remarkably improved in the heat stability and aging stability.

Furthermore, in the polymerizable composition comprising the photosensitive composition of the present invention having added thereto a monomer having an ethylenically unsaturated bond, the organic borate salt can be remarkably improved in the heat stability and aging stability and moreover, the polymerizability of the composition is not impaired.

The photosensitive composition of the present invention exhibits high sensitivity even in the presence of oxygen and the polymerizable composition obtained by adding a monomer having an ethylenically unsaturated bond and a high molecular polymer to the photosensitive composition efficiently undergoes polymerization even in the presence of oxygen.

While the invention has been described in detail and with reference to specific embodiments thereof, it will be apparent to one skilled in the art that various changes and modifications can be made therein without departing from the spirit and scope thereof.

What is claimed is:

1. A photosensitive composition comprising (A) a stabilizer selected from the group consisting of (i) a compound having a primary, secondary or tertiary amino group, and (ii) a compound having a thiol group, and (B) an organic borate salt represented by formula (1):

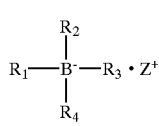

(1)

wherein $R_1$, $R_2$, $R_3$ and $R_4$ each independently represents an alkyl group, an aryl group, an allyl group, an aralkyl group, an alkenyl group, an alkynyl group, an alkoxy group, a silyl group, an alicyclic group a heterocylic group, a hydrogen atom or a halogen atom, and $Z^+$ represents a quaternary ammonium cation, a quaternary pyridinium cation, a quaternary quinolinium cation, a phosphonium cation, a sulfonium cation, an oxosulfonium cation, an oxonium cation, or an iodonium cation.

2. The photosensitive composition as claimed in claim 1, wherein, in formula (1), $R_1$, $R_2$, $R_3$ and $R_4$ each independently represents an alkyl group, an aryl group, an allyl group, an aralkyl group, an alkenyl group, an alkynyl group, an alkoxy group, a silyl group, a heterocyclic group, a hydrogen atom or a halogen atom, and $Z^+$ represents a quaternary ammonium cation, a quaternary pyridinium cation, a quaternary quinolinium cation, a phosphonium cation, a sulfonium cation, an oxonium cation, or an iodonium cation.

3. The photosensitive composition as claimed in claim 1, further comprising a sensitizing dye.

4. The photosensitive composition as claimed in claim 1, which further contains a bisimidazole compound.

5. A polymerizable composition capable of polymerization by light or heat, comprising the photosensitive composition described in claim 1 having added thereto at least one monomer having one or more ethylenically unsaturated bonds.

6. The polymerizable composition as claimed in claim 5, further comprising a high molecular polymer.

7. The polymerizable composition as claimed in claim 6, further comprising a pigment.

8. The polymerizable composition as claimed in claim 6, wherein the high molecular polymer has an acid value of from 20 to 800 mgKOH/g.

9. A colored pattern formed on a substrate using a polymerizable composition described in claim 5.

10. The photosensitive composition as claimed in claim 1, wherein the amount of the stabilizer (A) is 10 to 500 wt % of the organic borate salt (B).

11. A photosensitive composition comprising (A) a stabilizer selected from the group consisting of (i) a compound having a primary, secondary or tertiary amino group, and (ii) a compound having a thiol group, and (B) an organic borate salt represented by formula (1):

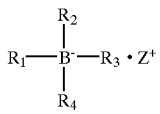
(1)

wherein $R_1$, $R_2$, $R_3$ and $R_4$ each independently represents an alkyl group, an aryl group, an allyl group, an aralkyl group, an alkenyl group, an alkynyl group, an alkoxy group, a silyl group, an alicyclic group, a heterocyclic group, a hydrogen atom or a halogen atom, and $Z^+$ represents a quaternary ammonium cation, a quaternary pyridinium cation, a quaternary quinolinium cation, a phosphonium cation, a sulfonium cation, an oxosulfonium cation, an oxonium cation, or an iodonium cation, wherein the compound having a primary, secondary or tertiary amino group is an amine represented by formula (2):

$$R_5R_6R_7N \qquad (2)$$

wherein $R_5$, $R_6$ and $R_7$ each independently represents hydrogen, an alkyl group, an aryl group, an allyl group, an aralkyl group, an alkenyl group, an alkynyl group, an alicyclic group or a heterocyclic group, provided that at least one of $R_5$, $R_6$ and $R_7$ is not a hydrogen; two or three of $R_5$, $R_6$ and $R_7$ may be combined to form a cyclic structure.

12. The photosensitive composition as claimed in claim 11, wherein, in formula (1), $R_1$, $R_2$, $R_3$ and $R_4$ each independently represents an alkyl group, an aryl group, an allyl group, an aralkyl group, an alkenyl group, an alkynyl group, an alkoxy group, a silyl group, a heterocyclic group, a hydrogen atom or a halogen atom, and $Z^+$ represents a quaternary ammonium cation, a quaternary pyridinium cation, a quaternary quinolinium cation, a phosphonium cation, a sulfonium cation, an oxonium cation, or an iodonium cation.

13. The photosensitive composition as claimed in claim 11, further comprising a sensitizing dye.

14. The photosensitive composition as claimed in claim 11, which further contains a bisimidazole compound.

15. A polymerizable composition capable of polymerization by light or heat, comprising the photosensitive composition described in claim 11 having added thereto at least one monomer having one or more ethylenically unsaturated bonds.

16. The polymerizable composition as claimed in claim 15, further comprising a high molecular polymer.

17. The polymerizable composition as claimed in claim 16, further comprising a pigment.

18. The polymerizable composition as claimed in claim 16, wherein the high molecular polymer has an acid value of from 20 to 800 mgKOH/g.

19. A colored pattern formed on a substrate using a polymerizable composition described in claim 15.

20. The photosensitive composition as claimed in claim 11, wherein the amount of the stabilizer (A) is 10 to 500 wt % of the organic borate salt (B).

21. A photosensitive composition comprising (A) a stabilizer selected from the group consisting of (i) a compound having a primary, secondary or tertiary amino group, and (ii) a compound having a thiol group, and (B) an organic borate salt represented by formula (1):

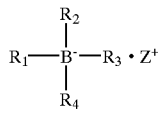
(1)

wherein $R_1$, $R_2$, $R_3$ and $R_4$ each independently represents an alkyl group, an aryl group, an allyl group, an aralkyl group, an alkenyl group, an alkynyl group, an alkoxy group, a silyl group, an alicyclic group, a heterocyclic group, a hydrogen atom or a halogen atom, and $Z^+$ represents a quaternary ammonium cation, a quaternary pyridinium cation, a quaternary quinolinium cation, a phosphonium cation, a sulfonium cation, an oxosulfonium cation, an oxonium cation, or an iodonium cation, wherein the compound having a thiol group is a thiol represented by formula (3):

$$R_8\text{—SX} \qquad (3)$$

wherein $R_8$ represents an alkyl group, an aryl group, an aralkyl group, an alkenyl group, an alkynyl group, an alicyclic group or a heterocyclic group, and X represents sodium or a hydrogen atom.

22. The photosensitive composition as claimed in claim 21, wherein, in formula (1), $R_1$, $R_2$, $R_3$ and $R_4$ each independently represents an alkyl group, an aryl group, an allyl group, an aralkyl group, an alkenyl group, an alkynyl group, an alkoxy group, a silyl group, a heterocyclic group, a hydrogen atom or a halogen atom, and $Z^+$ represents a quaternary ammonium cation, a quaternary pyridinium cation, a quaternary quinolinium cation, a phosphonium cation, a sulfonium cation, an oxonium cation, or an iodonium cation.

23. The photosensitive composition as claimed in claim 21, further comprising a sensitizing dye.

24. The photosensitive composition as claimed in claim 21, which further contains a bisimidazole compound.

25. A polymerizable composition capable of polymerization by light or heat, comprising the photosensitive composition described in claim 21 having added thereto at least one monomer having one or more ethylenically unsaturated bonds.

26. The polymerizable composition as claimed in claim 25, further comprising a high molecular polymer.

27. The polymerizable composition as claimed in claim 26, further comprising a pigment.

28. The polymerizable composition as claimed in claim 26, wherein the high molecular polymer has an acid value of from 20 to 800 mgKOH/g.

29. A colored pattern formed on a substrate using a polymerizable composition described in claim 25.

30. The photosensitive composition as claimed in claim 21, wherein the amount of the stabilizer (A) is 10 to 500 wt % of the organic borate salt (B).

31. A process for stabilizing an organic borate salt represented by formula (1):

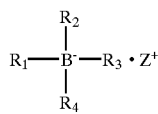

(1)

wherein $R_1$, $R_2$, $R_3$ and $R_4$ each independently represents an alkyl group, an aryl group, an allyl group, an aralkyl group, an alkenyl group, an alkynyl group, an alkoxy group, a silyl group, an alicyclic group, a heterocyclic group, a hydrogen atom or a halogen atom, and $Z^+$ represents a quaternary ammonium cation, a quaternary pyridinium cation, a quaternary quinolinium cation, a phosphonium cation, a sulfonium cation, an oxosulfonium cation, an oxonium cation, an iodonium cation, a metal cation or a cationic dye with absorption in the ultraviolet and/or visible ray region;

the process comprising the steps of:
  preparing a solvent in which the organic borate salt is dissolved, and
  dissolving in the solvent a stabilizer selected from the group consisting of (i) a compound having a primary, secondary or tertiary amino group, (ii) a compound having a thiol group, and (iii) a compound having one or two nitrogen-containing 5- or 6-membered heterocyclic rings having a double bond within the ring.

32. The process according to claim 31, wherein the stabilizer is dissolved in the solvent in an amount of 10 to 500 wt % based on the organic borate salt.

* * * * *